United States Patent
Hourcade et al.

(10) Patent No.: US 6,197,131 B1
(45) Date of Patent: Mar. 6, 2001

(54) METHOD FOR CONTROLLING THE BEHAVIOR OF A STEEL IN AN $H_2S$ MEDIUM

(75) Inventors: Martine Hourcade, Paris; Patrice Lefrancois, Cormeilles en Parisis; Xavier Longaygue, Noisy le Grand, all of (FR)

(73) Assignee: Institute Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/103,527

(22) Filed: Jun. 24, 1998

(30) Foreign Application Priority Data

Jun. 24, 1997 (FR) .................................................. 97 07978

(51) Int. Cl.[7] ...................................................... C12D 6/00
(52) U.S. Cl. .............................................................. 148/508
(58) Field of Search .................................... 148/508, 595, 148/662, 663

(56) References Cited

U.S. PATENT DOCUMENTS 5,213,637   5/1993   Mallen Herrero et al. .......... 148/598

FOREIGN PATENT DOCUMENTS 2 686 978   8/1993   (FR) .

OTHER PUBLICATIONS

Patents Abstracts of Japan, vol. 18, No. 92, (P–1693), Feb. 15, 1994 (JP 5 297181 A), Nov. 12, 1993.

Database WPI, AN 84–099252 [16], Jul. 7, 1983 (SU 1 027 585 A).

*Primary Examiner*—Deborah Yee
(74) *Attorney, Agent, or Firm*—Millen, White, Zelano & Branigan, P.C.

(57) ABSTRACT

The present invention relates to a method for predicting and controlling the hydrogen corrosion and embrittlement behavior of steels in the presence of $H_2S$. In the method, at least the following stages are carried out: determining a characteristic value $l_0$ which is a function of the proportion of dislocations present in the lattice of a first steel sample treated under hardening conditions such that, after the hardening treatment, by quenching and tempering or by work hardening, the hardness of said steel reaches a maximum value at a threshold stress $\sigma_{threshold}$ such that $\sigma_{threshold}$ equals $k \cdot R_{p0.2}$ k being less than or equal to $Rp_{0.2}$ of said steel; determining a characteristic value $l_1$ which is a function of the proportion of dislocations present in the lattice of a second treated steel sample; and comparing $l_1$ and $l_0$, and if $l_1$ is less than or equal to $l_0$, the treated steel of the second sample is said to be non sensitive to hydrogen corrosion and embrittlement in the presence of $H_2S$ according to the criterion defined by the value of k. When the resultant steel has a value $l_1$ less than $l_0$, the resultant steel can be used for the armouring of wires, for example.

22 Claims, 1 Drawing Sheet

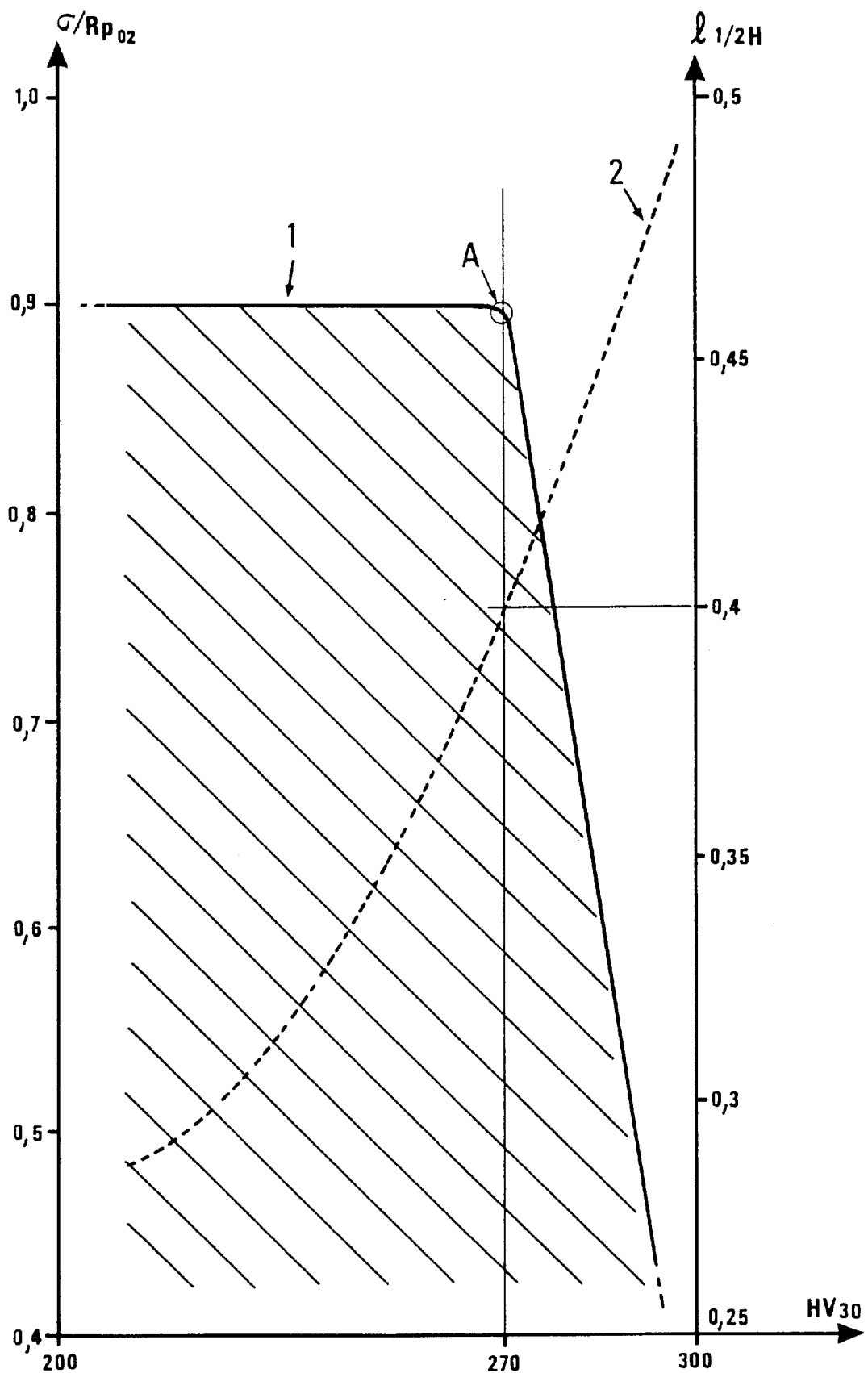

METHOD FOR CONTROLLING THE BEHAVIOR OF A STEEL IN AN H₂S MEDIUM

FIELD OF THE INVENTION

The object of the present invention relates to the field of analysis of the hydrogen stress corrosion and embrittlement resistance of a steel in the presence of an acid medium containing $H_2S$. The present invention notably applies to the process of manufacturing flexible pipes comprising wires that form mechanical pressure or tensile strength armourings.

In the case of the manufacture of flexible pipes intended to work in the presence of $H_2S$, the quality of the steels used for manufacturing armouring wires, as well as the mechanical and thermal treatments, must be so selected that these wires provide the mechanical strength that is indispensable during operation, while withstanding hydrogen corrosion and embrittlement that can be generated by the presence of $H_2S$.

BACKGROUND OF THE INVENTION

Prior works have allowed to establish that there is a correlation between the resistance to corrosion in the presence of $H_2S$ and the hardness of the metal. It has been determined that carbon steels and/or low-alloy steels having a hardness lower than or equal to 22 HRC have a good corrosion strength in the presence of $H_2S$. It has therefore been decided to characterize steel by its HRC hardness. The NACE/MR-0175 standard lays down that the carbon steels used in the petroleum field are considered to be compatible with $H_2S$ if they have a hardness below 22 HRC, the carbon contents being less than or equal to 0.38%. Considering the correspondence between the HRC hardness and the tensile strength Rm, this mode of characterization leads to select steels allowing to obtain products of strength Rm lower than about 800 MPa. It is clear that this can lead to non-optimized armouring wire dimensions. However, the NACE/MR-0175 standard provides for the case of low-alloy, hardened and tempered steels that do not meet the hardness requirement of less than 22 HRC. In this case, these steels must be capable of withstanding corrosion under stress σ in an $H_2S$ medium (NACE/TM01-77 standard). A test performed on a representative sample will allow to check that steels in this state can be used for the manufacture of metal structures that must withstand the effects of stress corrosion in an $H_2S$ medium. The stress $\sigma_{threshold}$ beyond which test TM01-77 is not satisfied also has to be determined. It needs to be known that a test TM01-77 (commonly referred to as SSCC for Sulfide Stress Corrosion Cracking) lasts for about 30 days, which is not comparable to a hardness type characterization test.

A faster method than steel characterization tests TM01-77 is therefore required.

SUMMARY OF THE INVENTION

The present invention thus relates to a method for controlling the hydrogen corrosion and embrittlement behaviour of steels in the presence of $H_2S$ wherein at least the following stages are carried out:

determining a characteristic value $l_0$ which is a function of the proportion of dislocations present in the lattice of a first steel sample treated under such conditions that, after treatment, the mechanical characteristics of the steel reach a maximum value and have a threshold stress $\sigma_{threshold}$ such that $\sigma_{threshold} = k \cdot Rp_{0.2}$, k being less than or equal to 1, $\sigma_{threshold}$ being defined hereafter, determining a characteristic value $l_1$ which is a function of the proportion of dislocations present in the lattice of a second treated steel sample, comparing $l_1$ and $l_0$. If $l_1$ is less than or equal to $l_0$, the treated steel of the second sample is said to be non sensitive to hydrogen corrosion and embrittlement in the presence of $H_2S$ according to the criterion defined by the value of k.

In the method, at least one of the first and second sample can be treated by quenching and tempering.

At least one of the first and second sample can be treated by work hardening.

The hardening treatment can lead to a mixed bainite/martensite structure or even to a mixed bainite/martensite/ferrite structure.

The hardening treatment can also lead to a mainly bainitic structure.

The second sample can be subjected to a different tempering treatment than the first sample.

The steel of the samples can be selected from a carbon steel and a low-alloy steel.

The steel of the second sample can have a different carbon content than the first sample, the nature and the composition of the other alloy elements being substantially identical.

The value of coefficient k can be about 0.9.

The characteristic value of the proportion of dislocations can be obtained by X-ray cristallography and correspond to the width at half height ($l_{1/2}$ evaluated in angle degree) of the X-ray diffraction peak corresponding to a line Kα of the ferrite.

The value of $l_0$ can be about 0.4° for the quenched and tempered steels of the CD4 family.

The present invention can be advantageously applied for controlling the quality of the tempering treatment for a similar steel composition.

The method can also be applied for controlling the quality of a sample comprising a weld.

Other features and advantages of the present invention will be clear from reading the non limitative examples hereafter, notably illustrated by the accompanying figure which shows, for a given steel, the zones of non-sensitivity to SSCC (according to the TM01-77 standard) as a function of the threshold stress and of the hardness.

DETAILED DESCRIPTION

The examples hereafter have been dealt with for a family of various steels whose nature and composition are given in Table 1. This chromium-molybdenum family comprises steels of very similar alloy compositions in a carbon content range of between about 0.12% and 0.42%, which can reach 0.65% (AISI 4161).

TABLE 1

| Grades | | | Chemical composition (%) | | | | | | | |
|---|---|---|---|---|---|---|---|---|---|---|
| EURONORM | AFNOR | AISI | C | Si | Mn | S | P | Ni | Cr | Mo |
| 12CrMo4KD | 12CD4 | 4112 | 0.132 | 0.30 | 0.81 | <0.003 | <0.009 | — | 0.96 | 0.20 |
| 25CrMo4KD | 25CD4 | 4125 | 0.255 | 0.21 | 0.63 | <0.003 | 0.10 | 0.17 | 1.11 | 0.21 |
| 34CrMo4KD | 35CD4 | 4135 | 0.335 | 0.28 | 0.73 | <0.003 | <0.009 | 0.11 | 1.03 | 0.18 |
| 42CrMo4KD | 42CD4 | 4142 | 0.399 | 0.26 | 0.64 | <0.003 | 0.009 | — | 0.98 | 0.22 |

The samples are hardened, after austenitization, so as to obtain a substantially 100% martensitic structure. The samples are subjected to a thermal tempering treatment with different temperature and time conditions. For each tempering condition pair (temperature-time), at least the Vickers hardness is measured with a load of 30 kg (HV30) and the conventional elastic limit at 0.2%: $Rp_{0.2}$ (MPa).

According to the TM01-77 test standard, the threshold stress $\sigma_{threshold}$ below which the sample does not break after 720 h and above which it breaks is determined.

In the present case, the following threshold of non-sensitivity to SSCC is also taken: $\sigma_{threshold}=0.9 \cdot Rp_{0.2}$, which means that the threshold stress according to the definition above is taken equal to $0.9 \cdot Rp_{0.2}$ when this loading stress does not lead to more than two breakages in five tests during the TM01-77 test.

The results are shown in Tables 2, 3, 4 and 5.

TABLE 2

35CD4

| | RX | Mechanical tests | | SCC test | |
|---|---|---|---|---|---|
| Thermal treatment file | $l_{1/2H}$ (FWHM) | Hardness HV30 | $Rp_{0.2\%}$ (MPa) | $\alpha_{threshold}$ (MPa) | $\alpha_{threshold}/Rp_{0.2\%}$ |
| Water quenching followed by tempering at 685° C. | | | | | |
| 8 min | 0.4289 | 278 | 772 | <540 | <0.7 |
| 15 min | 0.4101 | 275 | 755 | 603 | 0.8 |
| 30 min | 0.3956 | 268 | 733 | 660 | 0.9 |
| 1 h | 0.3587 | 256 | 695 | 625 | 0.9 |
| 8 h | 0.2910 | 219 | 581 | 523 | 0.9 |
| 655° C. | | | | | |
| 0 h 30 | 0.4599 | 287 | 793 | <555 | <0.7 |
| 1 h | 0.4213 | 278 | | <535 | <0.7 |
| 2 h | 0.3970 | 267 | 732 | 661 | 0.9 |
| 625° C. | | | | | |
| 1 h | 0.4970 | 297 | 832 | <499 | <0.6 |
| 2 h | 0.4621 | 289 | 806 | <564 | <0.7 |
| 4 h | 0.4355 | 281 | 782 | 546 | 0.7 |
| 8 h 20 | 0.4019 | 268 | 738 | 664 | 0.9 |

TABLE 3

12CD4

| | RX | Mechanical tests | | SCC tests | |
|---|---|---|---|---|---|
| Thermal treatment file | $l_{1/2H}$ (FWHM) | Hardness HV30 | $Rp_{0.2\%}$ (MPa) | $\alpha_{threshold}$ (MPa) | $\alpha_{threshold}/Rp_{0.2\%}$ |
| Round samples (diameter 7 mm) quenched in salt water tempered at 640° C. | | | | | |
| 1 h | 0.4139 | 234 | 680 | 612 | ≦0.8 |
| | | | | 630 | <0.9 |
| 2 h | 0.3844 | 227 | 671 | 604 | 0.9 |

TABLE 4

25CD4

| | RX | Mechanical tests | | SCC test | |
|---|---|---|---|---|---|
| Thermal treatment file | $l_{1/2H}$ (FWHM) | Hardness HV30 | $Rp_{0.2\%}$ (MPa) | $\alpha_{threshold}$ (MPa) | $\alpha_{threshold}/Rp_{0.2\%}$ |
| Water quenching followed by tempering at 655° C. | | | | | |
| 1 h | 0.4249 | 264 | 743 | 668 | ≦0.8 |
| 2 h | 0.4006 | 252 | 714 | 643 | 0.9 |

TABLE 5

42CD4

| | RX | Mechanical tests | | SCC test | |
|---|---|---|---|---|---|
| Thermal treatment file | $l_{1/2H}$ (FWHM) | Hardness HV30 | $Rp_{0.2\%}$ (MPa) | $\alpha_{threshold}$ (MPa) | $\alpha_{threshold}/Rp_{0.2\%}$ |
| Water quenching followed by tempering at 680° C. | | | | | |
| 1 h | 0.4442 | 282 | 759 | 683 | ≦0.8 |
| 2 h | 0.3775 | 268 | 730 | 657 | 0.9 |

BRIEF DESCRIPTION OF THE DRAWING

By means of the various measurements performed on 35CD4 steel samples, the curves of FIG. 1 are drawn, curve 1 representing the boundary between the breaking zone and the non-breaking zone. The non-breaking zone is the hatched zone. The boundary is defined by the locus of a point where:

loading stress σ does not lead to a breakage during a TM01-77 test, or stress σ is at least $0.9 \cdot Rp_{0.2}$.

DETAILED DESCRIPTION OF THE DRAWING

Curve 1 is drawn with $\sigma/Rp_{0.2}$ (ordinate) as a function of the hardness HV30 (abscissa). The plateau at $0.9 \cdot Rp_{0.2}$ represents the boundary between the hatched lower zone where no breakage occurs and the upper zone that has not been explored since the stress of the NACE test is at least $0.9 \cdot Rp_{0.2}$. Point A is the point where the hardening of the sample reaches a maximum value considering the SSCC resistance criteria and the coefficient k of 0.9 selected.

For hardnesses below about 270 HV30, the threshold stress is at least $0.9 \cdot Rp_{0.2}$.

For the type of steels considered, one seeks the thermal treatment leading to a given $Rp_{0.2}$ (and hardness) for which curve 1 decreases, which corresponds to point A where the threshold stress becomes less than $0.9 \cdot Rp_{0.2}$. So far, for 100% martensitic tempered structures, considering the direct relation between the elastic limit $Rp_{0.2}$ and the hardness, point A is characterized by the hardness, whose value is here 270 HV30.

The use of FIG. 1 can be summarized as follows: for the given steel (35CD4 here), the thermal treatments leading to a hardness that is less than or equal to 270 HV30 are suitable as regards hydrogen corrosion and embrittlement in the presence of $H_2S$, for the set threshold stress criterion of at least $0.9 \cdot Rp_{0.2}$.

The hardness parameter includes two main components:
- the precipitation of carbides (size, number per unit of volume, distribution, nature and crystallographic coherence with the matrix, etc.),
- residual dislocations after tempering (nature, density).

These two elements, which take part in the hardening, are traps of different natures of hydrogen. Carbides are rather high interaction energy traps whereas dislocations are traps of lower energy likely to supply hydrogen to dangerous defects (and reach therein the critical concentration that leads to the breaking of the material).

During tempering, the precipitation of carbides develops and the proportion of dislocations decreases, all the more so as tempering reaches an advanced level.

The proportion of dislocations present in the lattice, after tempering of the 100% martensitic structure, can be estimated by means of a specific X-ray crystallography measurement (Debye-Scherrer method). This measurement can characterize the hydrogen embrittlement behaviour of the material.

Each sample treated, studied from the viewpoint of its SSCC resistance, has been examined by X-ray diffraction. X-ray diffraction allows, by means of a fine analysis of the diffractogram, to access a measurement in connection with the proportion of dislocations present in a material. In fact, a material containing a great number of dislocations consists of phases whose crystalline parameters are not identical from one point of the crystal to another, due to the lattice distortions induced by the stresses and the dislocations. Consequently, the diffraction peak of a family of reticular planes of a given phase, a peak whose angular position $\theta$ in the diffractogram depends on the inter-reticular distance d of the family of planes considered according to Bragg's law $\lambda = 2d\sin\theta$ (where $\lambda$ is the wavelength of the incident X ray), is all the wider as the stress level, and therefore the lattice distortion level, is higher.

The method thus consists here in measuring the width at half height of the diffraction peak of the ferrite $\alpha$ on a line $K\alpha$. From the recording of the diffractogram, a software performs the deconvolution between the lines and computes thereafter the width at half height ($l_{1/2}H$), expressed in angle degree, of the peak. The hardness (HV30)—width at half height ($l_{1/2}H$) pair is shown in FIG. 1 by curve 2. Matching of the various measurements of $l_{1/2}H$, of the hardness HV30 and of the SSCC resistance has allowed to notice that, when $l_{1/2}H$ is substantially less than or equal to 0.4°, the SSCC behaviour of the material is good according to the criterion previously defined.

The results presented in Tables 2 to 5 show that, for a family of (100% martensitic) hardened steels (12CD4, 25CD4, 35CD4 and 42CD4) and for different tempered states, the 0.4° critical value, which ensures a good SSCC behaviour, is substantially the same. These results confirm that the proportion of dislocations present in a lattice of a treated material, notably hardened and tempered, can characterize the behaviour of the material during SSCC tests according to the TM01-77 standard. The present invention preferably uses X-ray crystallography rather than other possible methods for evaluating the proportion of dislocations.

The present invention shows that a measurement readily obtained by X-ray diffraction allows to ensure that a material treated notably by hardening and tempering has a good SSCC behaviour. In the present example, determining the value of the measurement of the width at half height of the diffraction peak corresponding to a line of the ferrite is sufficient. For the family of steels considered, said value is about 0.04° with the calculating method and the sample preparation range used.

It is clear that, in relation to SSCC tests, the expected time and cost gain is very high with this method: the time elapsed between sampling and the result of the X-ray measurement is not more than a half day. In order to validate a tempered state, at least three SSCC tests that last for one month are generally required. Once the value of $l_{1/2}H$ for a given family of steels has been validated, X-ray measurements or equivalent measurements are sufficient to control the quality of the thermal treatment.

Furthermore, showing the importance of a critical proportion of dislocations as regards the SSCC behaviour allows to consider other measurements characterizing the proportion of dislocations.

The nature of the deconvolution operation included in the software that processes the data is important as regards the absolute value of the measurement. It is well-known that there are several deconvolution softwares. Calibration of the method must be performed for each deconvolution model.

The polished samples examined by X-rays must be prepared according to a reproducible procedure. Calibration of the critical value $l_{1/2}H$ in relation to the preparation conditions might be indispensible.

It can be noted that measurement can be performed on various lines of the ferrite or possibly on a line of another phase. Of course, the critical value $l_{1/2}H$ will be different. The texture of the material can also notably influence the critical value $l_{1/2}H$. For other higher alloy steels, the measurement of $l_{1/2}H$ will be different. Calibration will also be required in this case.

This method of preselecting the structural states of the materials by X-ray diffraction, which is based on the importance of the evaluation of the crystal lattice restoration rate in terms of residual dislocations, can be applicable, considering the physical laws on which this method is based, to:
- various hardened and tempered steels,
- various welded steels for weld control (with calibration),
- other hardened structures, martensite+bainite (+ferrite) for example,
- other steel treatments, other materials, with calibration of the method, work hardened states, notably after a thermal treatment or welding.

The preceding examples can be repeated with similar success by substituting the generically or specifically described reactants and/or operating conditions of this invention for those used in the preceding examples.

The entire disclosure of all applications, patents and publications, cited above and of corresponding French application 97/07978, are hereby incorporated by reference.

In the specification and claims, the value "$Rp_{0.2}$" is the conventional plastic limit measured at 0.2% of elongation (Yield strength at 0.2% offset ASTM-A370). Also, the "CD4 family" is a group of chromium-molybdenum steels of the family 41XX (AISI) having a carbon content of between 0.12% and 0.65% by weight.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for determining the susceptibility of steels to hydrogen corrosion and embrittlement behaviour in the presence of $H_2S$, comprising:

determining a characteristic value $l_0$ which is a function of the proportion of dislocations present in the lattice of a first steel sample treated under hardening conditions such that, after the hardening treatment, by quenching and tempering or by work hardening, the hardness of said steel reaches a maximum value at a threshold stress $\sigma_{threshold}$ such that $\sigma_{threshold}$ equals $k.R_{p0.2}$ k being less than or equal to $Rp_{0.2}$ of said steel, determining a characteristic value $l_1$ which is a function of the proportion of dislocations present in the lattice of a second treated steel sample, comparing $l_1$ and $l_0$, and if $l_1$ is less than or equal to $l_0$, the treated steel of the second sample is said to be non sensitive to hydrogen corrosion and embrittlement in the presence of $H_2S$ according to the criterion defined by the value of k.

2. A method as claimed in claim 1, wherein at least one of said first and second sample is treated by quenching and tempering.

3. A method as claimed in claim 1, wherein at least one of said first and second sample is treated by work hardening.

4. A method as claimed in claim 2, wherein the hardening treatment leads to at least one of the following structures: mainly bainitic, mixed bainite/martensite, mixed bainite/martensite/ferrite.

5. A method as claimed in claim 2, wherein the second sample has been subjected to a different tempering treatment than the first sample.

6. A method as claimed in claim 1, wherein the steel of said samples is selected from a carbon steel and a low-alloy steel.

7. A method as claimed in claim 1, wherein the steel of the second sample has a different carbon content than the first sample, the nature and composition of the other alloy elements being substantially identical.

8. A method as claimed in claim 1, wherein the value of k is about 0.9.

9. A method as claimed in claim 1, wherein said characteristic value of the proportion of dislocations is obtained by X-ray crystallography and corresponds to the width at half height ($l_{1/2}H$) of the X-ray diffraction peak corresponding to a line $K\alpha$ of the ferrite.

10. A method as claimed in claim 2, wherein the value of $l_0$ is about 0.4° for the crystallography and tempered steels of the CD4 family.

11. Applying the method as claimed in claim 2 to the quality control of said tempering treatment for a similar steel composition.

12. Applying the method as claimed in claim 1 to the quality control of a sample comprising a weld.

13. A method according to claim 1, further comprising manufacturing armouring wires from a resultant steel sample having a measured value l, less than or equal to $l_0$.

14. A method according to claim 2, further comprising manufacturing armouring wires from a resultant steel sample having a measured value l, less than or equal to $l_0$.

15. A method according to claim 3, further comprising manufacturing armouring wires from a resultant steel sample having a measured value l, less than or equal to $l_0$.

16. A method according to claim 4, further comprising manufacturing armouring wires from a resultant steel sample having a measured value l, less than or equal to $l_0$.

17. A method according to claim 5, further comprising manufacturing armouring wires from a resultant steel sample having a measured value l, less than or equal to $l_0$.

18. A method according to claim 6, further comprising manufacturing armouring wires from a resultant steel sample having a measured value l, less than or equal to $l_0$.

19. A method according to claim 7, further comprising manufacturing armouring wires from a resultant steel sample having a measured value l, less than or equal to $l_0$.

20. A method according to claim 8, further comprising manufacturing armouring wires from a resultant steel sample having a measured value l, less than or equal to $l_0$.

21. A method according to claim 9, further comprising manufacturing armouring wires from a resultant steel sample having a measured value l, less than or equal to $l_0$.

22. A method according to claim 10, further comprising manufacturing armouring wires from a resultant steel sample having a measured value l, less than or equal to $l_0$.

* * * * *

UNITED STATES PATENT AND TRADEMARK OFFICE
CERTIFICATE OF CORRECTION

PATENT NO. : 6,197,131 B1
DATED : March 6, 2001
INVENTOR(S) : Martine Hourcade, Patrice Lefrancois and Xavier Longaygue It is certified that error appears in the above-identified patent and that said Letters Patent is hereby corrected as shown below:

Column 8,
Line 16, after "the" delete "crystallography" and insert -- quenched --.

Signed and Sealed this

Seventh Day of May, 2002

Attest:

Attesting Officer

JAMES E. ROGAN
Director of the United States Patent and Trademark Office